United States Patent [19]

Summ

[11] Patent Number: 4,573,180
[45] Date of Patent: Feb. 25, 1986

[54] X-RAY DIAGNOSTIC APPARATUS WITH A COMPRESSION CARRIAGE

[75] Inventor: Herbert Summ, Wilhelmsdorf, Fed. Rep. of Germany

[73] Assignee: Siemens Aktiengesellschaft, Berlin and Munich, Fed. Rep. of Germany

[21] Appl. No.: 644,079

[22] Filed: Aug. 24, 1984

[30] Foreign Application Priority Data

Nov. 8, 1983 [DE] Fed. Rep. of Germany ... 8332063[U]

[51] Int. Cl.$^4$ ............................................. A01B 6/00
[52] U.S. Cl. ..................................... 378/037; 378/180; 378/195
[58] Field of Search ................. 378/177, 196, 195, 37, 378/179, 180

[56] References Cited

U.S. PATENT DOCUMENTS 4,259,585  3/1981  Novak et al. ......................... 378/37

OTHER PUBLICATIONS

Siemens, "Mammomat B", PIR87-022, Reg. ⅓, 6 pp.

Primary Examiner—Alfred E. Smith
Assistant Examiner—T. N. Grigsby
Attorney, Agent, or Firm—Mark H. Jay

[57] ABSTRACT

The invention concerns an X-ray diagnostic apparatus with a motor-driven, vertically adjustable compression carriage, a means of support for a compression plate, and with a support plate for the object photographed. A means of support for a second closer to the focus, support plate and two support locations for the compression plate are provided, of which one is associated with the support plate which can receive the X-ray film cassette, and the other with the support plate which is closer to the focus.

1 Claim, 1 Drawing Figure

U.S. Patent      Feb. 25, 1986      4,573,180
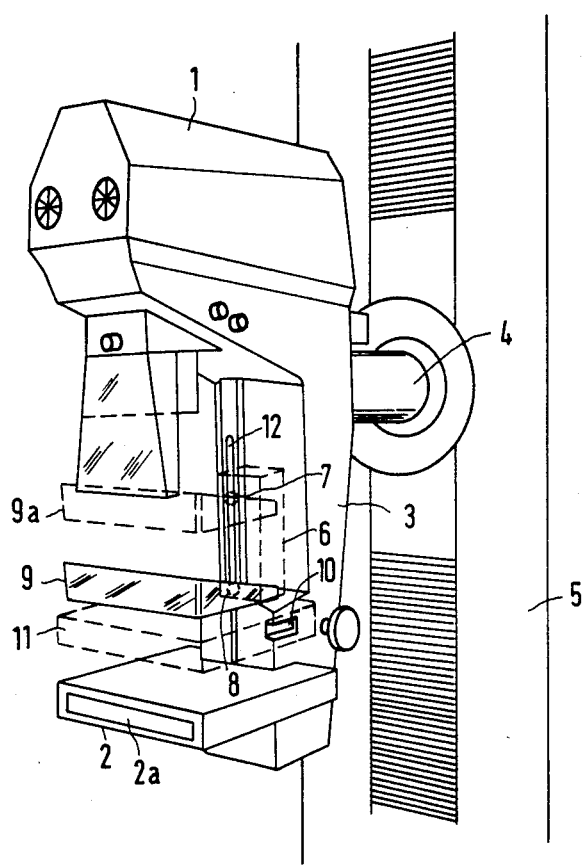

X-RAY DIAGNOSTIC APPARATUS WITH A COMPRESSION CARRIAGE

BACKGROUND OF THE INVENTION

The invention relates to an X-ray diagnostic apparatus with a compression carriage adjustable in a vertical direction by an electric motor, which supports a compression plate, and a support plate for the object to be photographed.

An X-ray diagnostic apparatus of this kind, which serves for preparation of photographs of the female breast, is known. The position of the compression plate with respect to the compression carriage is determined in such a way that, on the one hand, perfect positioning of the object to be photographed on the support plate is possible, because of the path available to the compression carriage and, on the other hand, perfect compression is also possible.

One object of the invention is to provide an X-ray diagnostic apparatus of the kind previously described which makes enlarged impressions possible, by which the photographed object is depicted enlarged on an X-ray film, whereby a reliable compression, at normal as well as for enlarged pictures, is ensured.

SUMMARY OF THE INVENTION

According to the invention, there is provided in the apparatus means of support for a second, closer to the focus, support plate and, on the compression carriage, two support locations for the compression plate, of which one is associated with the support plate which can receive the X-ray film cassette, and the other with the support plate which is closer to the focus.

In the X-ray diagnostic apparatus of the invention, two adjustment ranges are available for the compression plate along the adjustment path of the compression carriage. One is associated with the support plate for the X-ray cassette, the other with the support plate which is closer to the focus, for enlargement purposes.

BRIEF DESCRIPTION OF THE DRAWINGS

An illustrative and non-limiting preferred embodiment of the invention is illustrated in the single FIGURE.

DETAILED DESCRIPTION OF A PREFERRED EMBODIMENT

In the drawing, a housing 1 for an X-ray tube and a support plate 2 for preparation of mammographs of the usual type are shown. An X-ray film cassette 2a can be inserted into the support plate 2. The housing 1 and the support plate 2 are connected via a holder 3, which connects with a horizontal axle 4, with which it may be adjusted for height on a support 5. The unit 1, 2 can furthermore rotate about the axle 4.

In the holder 3, a motorized adjustable compression carriage 6 is provided, which has two openings 7, 8. In this example, a compression plate 9 is inserted with an attachment in the opening 8. If the photographed object is laid on the support plate 2, it can be compressed downward by the compression plate 9, by motorized adjustment.

For the preparation of enlarged X-ray images, a second support plate 11, which is closer to the focus than the support plate 2, can be attached to the holder 3. Enlargement takes place because the radiation from the X-ray tube is in the shape of a pyramid, and the greater the distance between the object to be photographed and the X-ray film cassette 2a, the greater the enlargement will be. By placing the object to be X-rayed upon the support plate 11, above the support plate 2, enlargement results, the degree of enlargement depending upon the distance between the support plate 11 and the support plate 2. Since a reliable compression is also possible in this case by the same adjustment path of the compression carriage 3, compression plate 9 is, in this case, located in the position shown with broken lines, indicated as 9a, inserted with its attachment in the opening 7 of the compression carriage. In each case, it lies over the second support plate 11, which is fastened to holder 3 by means of a projection 10 which is inserted in the holder 3. The compression plate 9, inserted into the openings 7, 8 with its pin, is adjustable length-wise in a slit 12 of the holder 3.

Those skilled in the art will understand that changes can be made in the preferred embodiments here described, and that these embodiments can be used for other purposes. Such changes and uses are within the scope of the invention, which is limited only by the claims which follow.

What is claimed is:

1. An X-ray diagnostic apparatus of the type having a source of X-rays having a focus, a vertically movable motor-driven compression carriage which supports a compression plate and a first support plate for an object to be X-rayed, comprising: a second support plate which is closer to the focus than the first support plate and means for mounting the compression plate in at least two positions, of which a first position is associated with the first support plate, and of which a second is associated with the second support plate.

* * * * *